United States Patent
Hu (12) 
(10) Patent No.: US 6,409,702 B1
(45) Date of Patent: Jun. 25, 2002

(54) PLUNGER AND NEEDLE HOLDER OF SAFETY HYPODERMIC SYRINGE

(75) Inventor: Chien-Kung Hu, Miao Li Hsien (TW)

(73) Assignees: Li-Hua Lu; Hung-Yang Fan; Chu-Chun Chiu, all of Miao Li Hsien (TW)

( * ) Notice: Subject to any disclaimer, the term of this patent is extended or adjusted under 35 U.S.C. 154(b) by 0 days.

(21) Appl. No.: 09/867,529

(22) Filed: May 31, 2001

(51) Int. Cl.[7] .................................................. A61M 5/00
(52) U.S. Cl. ........................................................ 604/110
(58) Field of Search ................................. 604/110, 228, 604/218, 187, 194–196

(56) References Cited

U.S. PATENT DOCUMENTS

| | | | | |
|---|---|---|---|---|
| 4,923,443 A | * | 5/1990 | Greenwood et al. | 604/110 |
| 5,211,628 A | * | 5/1993 | Marshall | 604/110 |
| 5,263,933 A | * | 11/1993 | Novacek et al. | 604/110 |
| 5,374,250 A | * | 12/1994 | Dixon | 604/110 |
| 5,378,240 A | * | 1/1995 | Curie et al. | 604/110 |
| 5,693,023 A | * | 12/1997 | Adams | 604/195 |
| 5,876,382 A | * | 3/1999 | Erickson | 604/198 |
| 5,899,887 A | * | 5/1999 | Liu | 604/195 |
| 6,193,695 B1 | * | 2/2001 | Rippstein, Jr. | 604/195 |

* cited by examiner

Primary Examiner—Sharon Kennedy
(74) Attorney, Agent, or Firm—Browdy and Neimark (57) ABSTRACT

A safety hypodermic syringe includes a barrel having a receiving hole, a needle holder slidably and controllably disposed therein and having an insertion hole, an inner tapered hole, a pull stop edge located between the insertion hole and the inner tapered hole, and a liquid transporting hole in communication with a hypodermic needle; a plunger having a rod body, a connection head of a conical shape cooperative with the inner tapered hole, two claws capable of retaining the pull stop edge of the needle holder, and two notches formed in opposite inner side of each claw; wherein the plunger and the needle holder are in intimate cooperation to provide a minimum residue of liquid drug, the claws serving to catch and pull the pull stop edge of the needle holder, so as to enable the plunger to draw the needle holder and the hypodermic needle into the receiving hole of said barrel.

10 Claims, 9 Drawing Sheets

PLUNGER AND NEEDLE HOLDER OF SAFETY HYPODERMIC SYRINGE

FIELD OF THE INVENTION

The present invention relates generally to a hypodermic syringe, and more particularly to an improvement on the plunger and the needle holder of the hypodermic syringe.

BACKGROUND OF THE INVENTION

For the sake of safety, the conventional hypodermic syringe comprises a hypodermic needle which can be drawn into the barrel by the plunger of the syringe after injection. However, such conventional hypodermic syringe is generally defective in design in that the needle holder is devoid of a good structural cooperation with the plunger, and that the needle holder often fails to be pulled back in by the plunger. In addition, the needle of the conventional hypodermic syringe does not meet the strict standard calling for minimum drug residue in the syringe after injection.

SUMMARY OF THE INVENTION

It is the primary objective of the present invention to provide a safety hypodermic syringe comprising a needle holder which can be drawn into the barrel by the plunger with precision.

It is another objective of the present invention to provide a safety hypodermic syringe comprising a needle holder and a plunger, which cooperate to reduce the drug residue after injection.

It is still another objective of the present invention to provide a safety hypodermic syringe with a simplified structure to engage the plunger and the needle holder of the hypodermic syringe.

The safety hypodermic syringe of the present invention comprises a barrel; a needle holder slidably disposed in a receiving hole of the barrel and provided with an insertion hole forming an inner tapered hole, a pull stop edge, a fluid transporting hole in communication with a hypodermic needle; a plunger having a rod body, a hooked connection head of a conical shape and corresponding to the inner tapered hole, two claws for retaining the pull stop edge of the needle holder, and two notches located in two sides thereof.

The plunger is capable of an intimate cooperation with the needle holder, thereby resulting in a reduction in the drug residue. The plunger is capable of drawing the needle holder into the barrel with precision after injection.

DETAILED DESCRIPTION OF THE INVENTION

Figure 1:
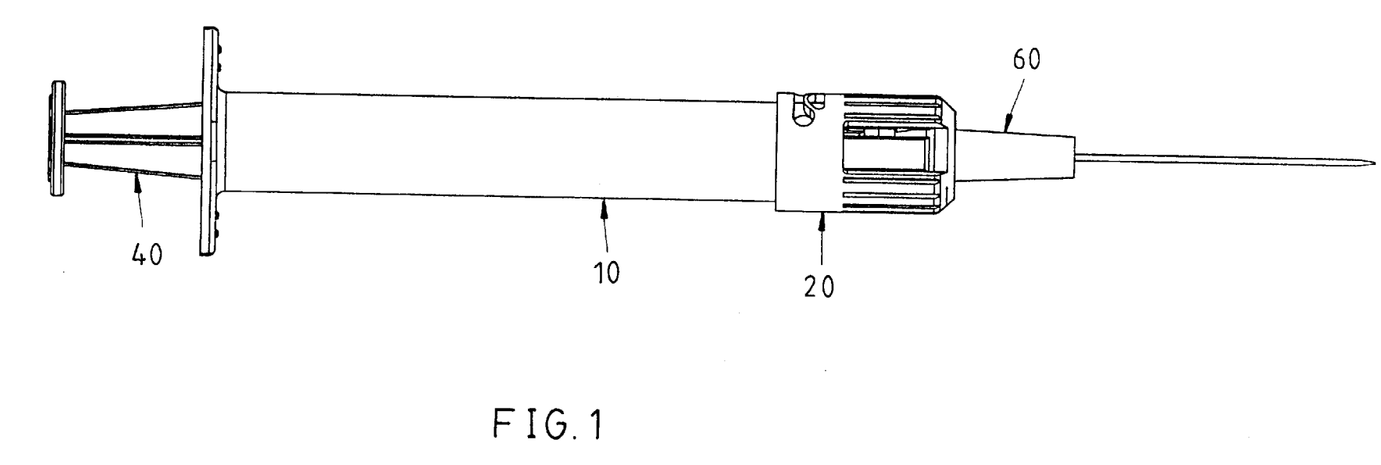
FIG. 1 shows a schematic plan view of a preferred embodiment of the present invention.
Figure 2:
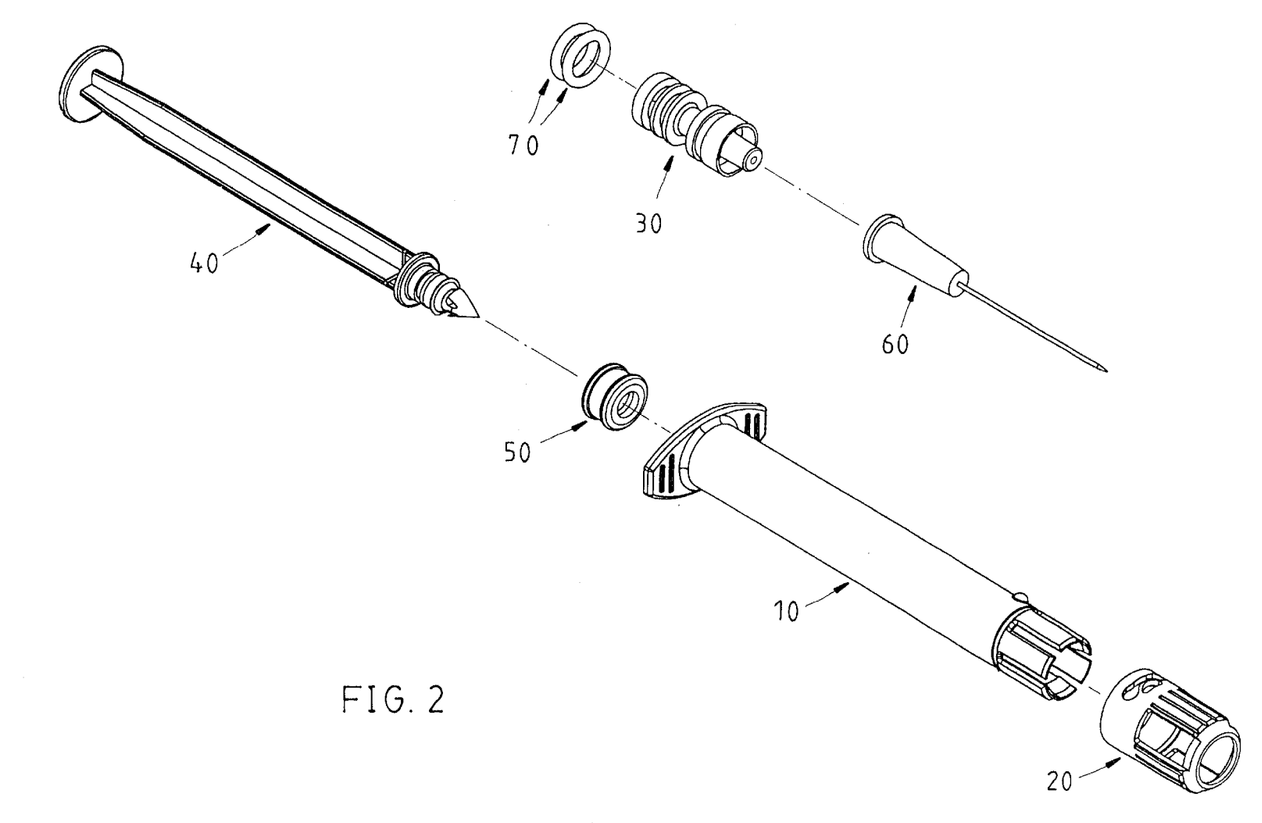
FIG. 2 shows an exploded view of the preferred embodiment of the present invention.
Figure 3:
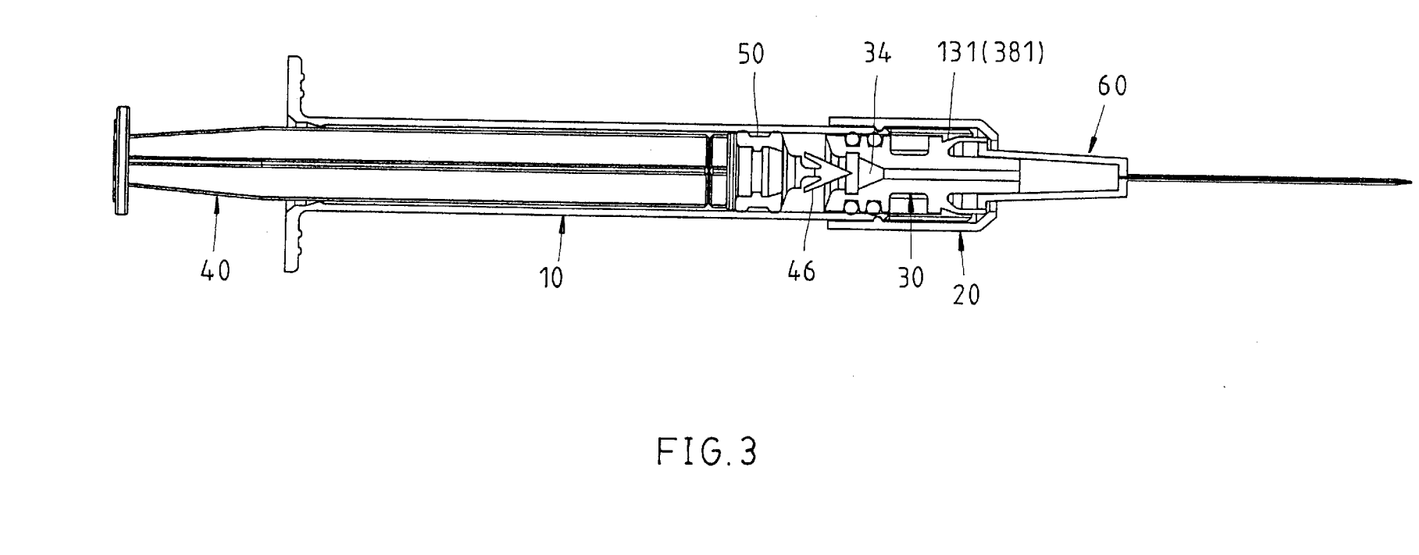
FIG. 3 shows a side sectional view of the preferred embodiment of the present invention prior to hypodermic injection.

As shown in FIGS. 1–3, a safety hypodermic syringe of the preferred embodiment of the present invention comprises the following component parts.

Figure 4:
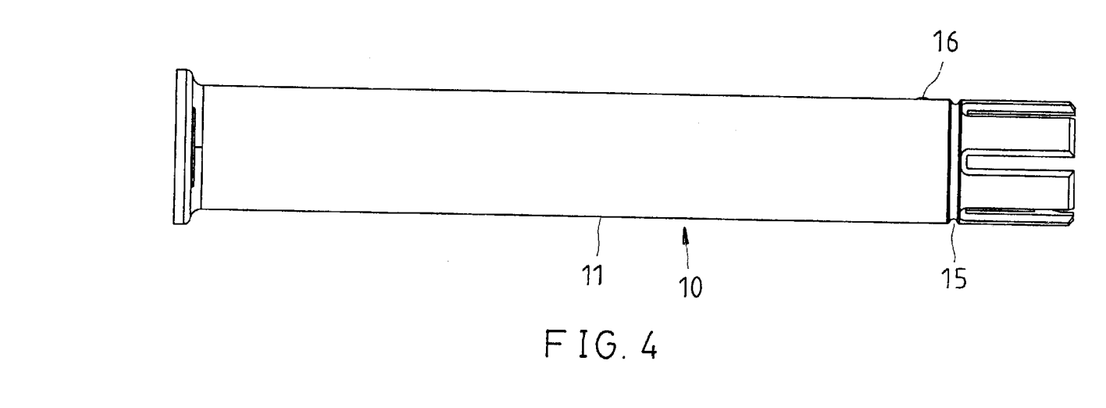
FIG. 4 shows a side view of a barrel of the preferred embodiment of the present invention.
Figure 5:
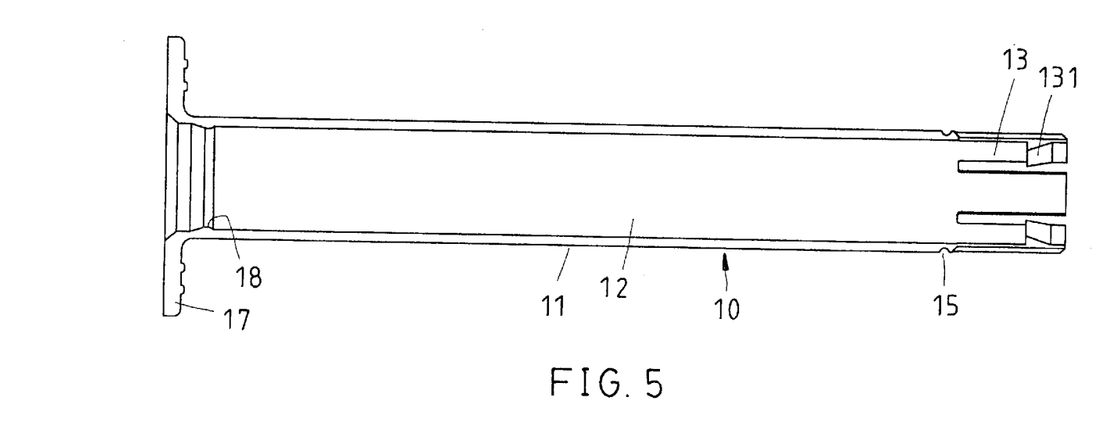
FIG. 5 shows a sectional view of the barrel of the preferred embodiment of the present invention.

As shown in FIGS. 4–5, a barrel 10 has a cylinder body 11, which is provided with a receiving hole 12, three catching pieces 13 arranged equidistantly in the circumference of the front end of the cylinder body 11 and provided in the inner edge with a retaining tooth 131, an outer circular groove 15 located at a predetermined position of the outer periphery, a locating projection 16 disposed at a predetermined position of the outer periphery of the cylinder body 11, a hand holding lug 17 disposed at other end of the cylinder body 11, a push rod stop edge 18 disposed in proximity of the opening of the receiving hole 12.

Figure 6:
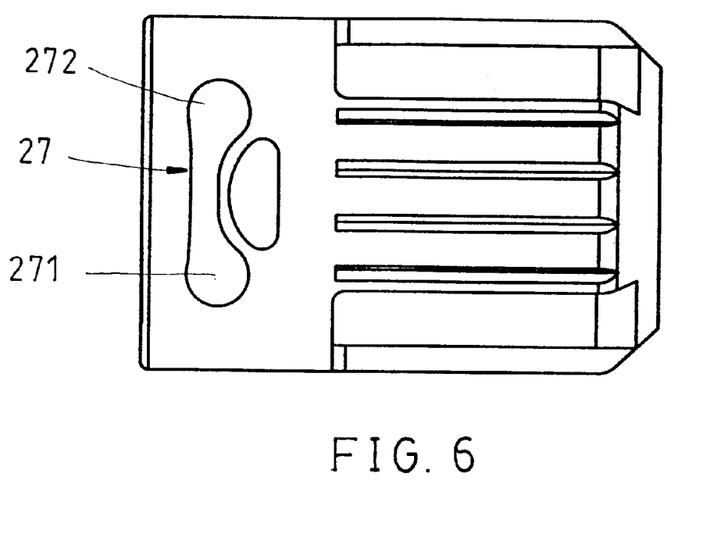
FIG. 6 shows a top view of an outer sleeve of the preferred embodiment of the present invention.
Figure 7:
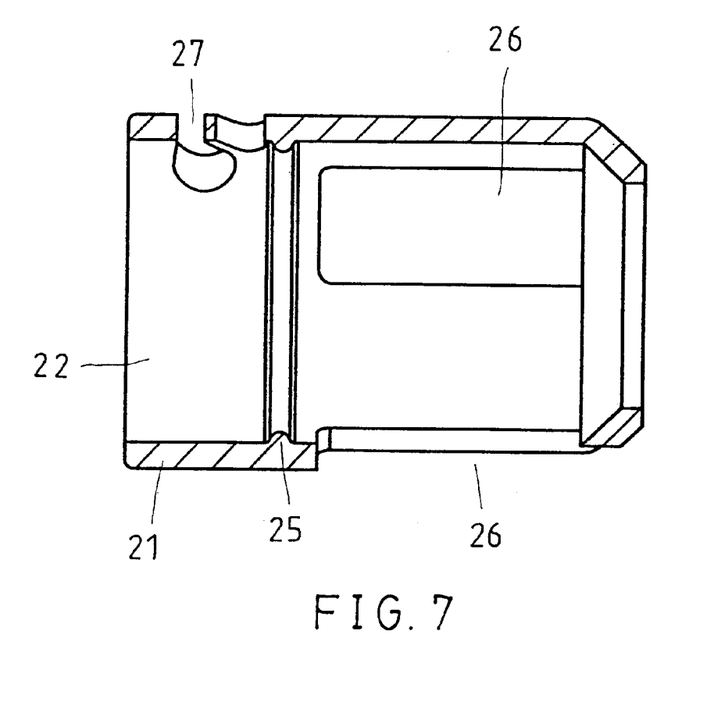
FIG. 7 shows a side sectional view of the outer sleeve of the preferred embodiment of the present invention.

As shown in FIGS. 6–7, an outer sleeve 20 has an annular body 21 which is axially provided with a fitting hole 22 for fitting with the cylinder body 11 of the barrel 10, an inner protruded ring 25 disposed at the inner edge of the fitting hole 22, three escape holes 26 arranged equiangularly in the front segment of the annular body 21, a locating slot hole 27 provided with a first hole 271, a second hole 272, and a projection slot channel 29 extending from the outer edge to the first hole 271.

Figure 8:
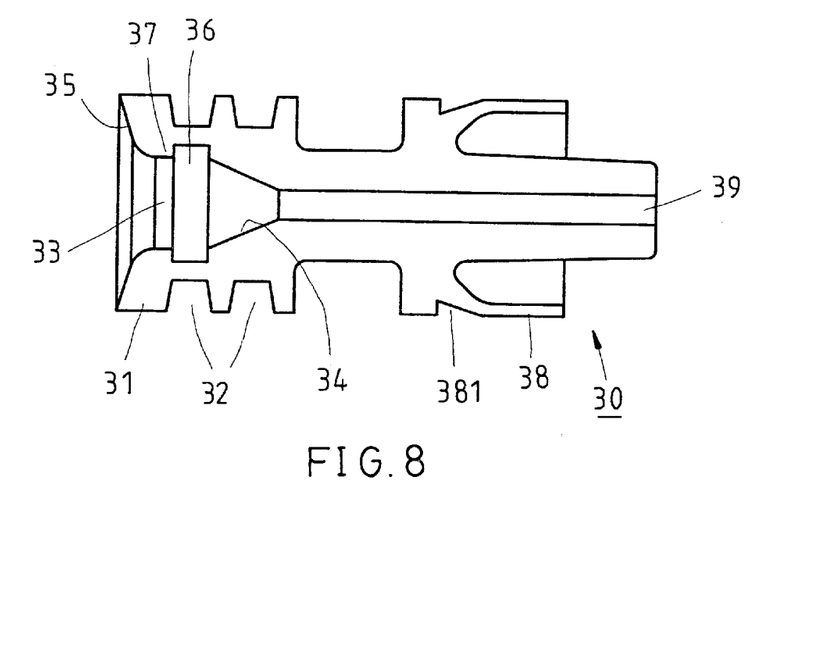
FIG. 8 shows a side sectional view of a needle holder of the preferred embodiment of the present invention.
Figure 9:
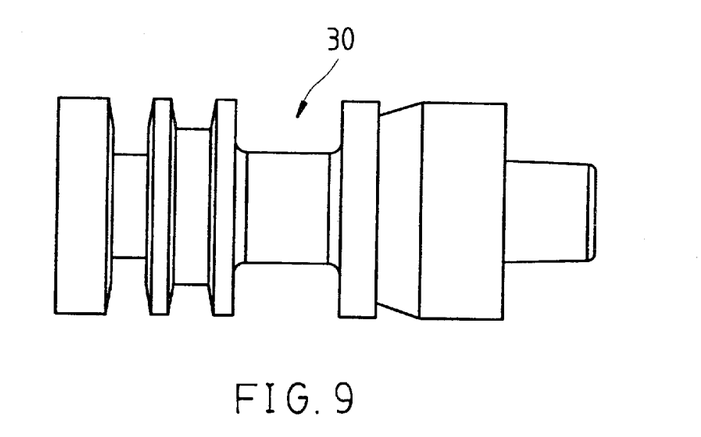
FIG. 9 shows an upper view of the needle holder of the preferred embodiment of the present invention.

As shown in FIGS. 8–9, a needle holder 30 has a cylinder cooperating portion 31, which is provided with two outer circular grooves 32 to accommodate two O rings and is capable of sliding in the receiving hole 12 of the barrel 10, an insertion hole 33 disposed inwards from the center, an inner tapered hole 34 disposed farther inward, a sunk hole 35 formed at the opening of the insertion hole 33, an open slot 36 communicating horizontally from the outer side with the insertion hole 33 and having two pull stop edges 37, a protective sleeve 38 disposed at the outer periphery of other end and provided with a retaining circular groove 381, and a liquid transporting hole 39 disposed axially.

Figure 10:
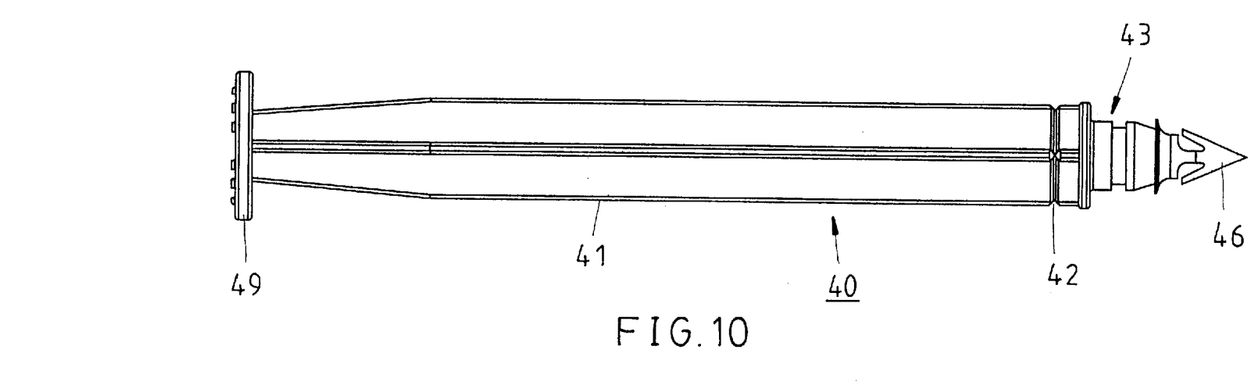
FIG. 10 shows a side view of a plunger of the preferred embodiment of the present invention.
Figure 11:
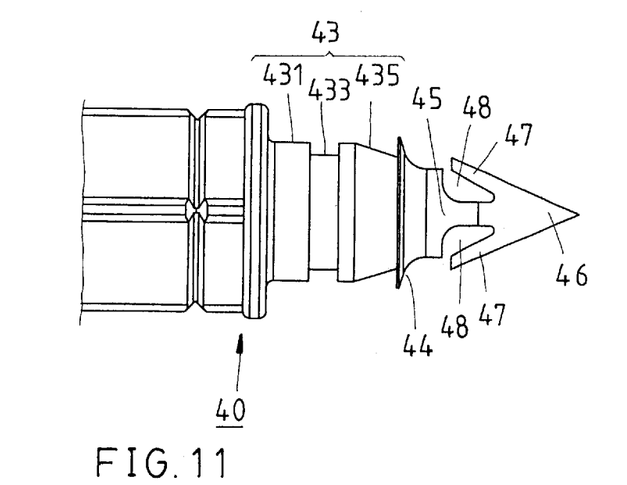
FIG. 11 shows a schematic view of a tip of the plunger of the preferred embodiment of the present invention.

As shown in FIGS. 10–11, a plunger 40 has a rod body 41 of a cruciform cross section, a severing portion 42 disposed at a predetermined position, a neck 43 connected at the front end and provided with a neck body 431, a recessed slot 433, and a tapered rod 435, a stop plug disk 44 disposed at farther front end, an insertion shaft body 45, a connection head 46 of a linear conical shape and corresponding to the inner tapered hole 34 of the needle holder 30, two claws 47 of a sectoral shape for retaining the pull stop edge 37 of the needle holder 30, two notches 48 formed at each side thereof, and a push disk 49 disposed at the rear end thereof to be pushed by finger.

Figures 12, 13:
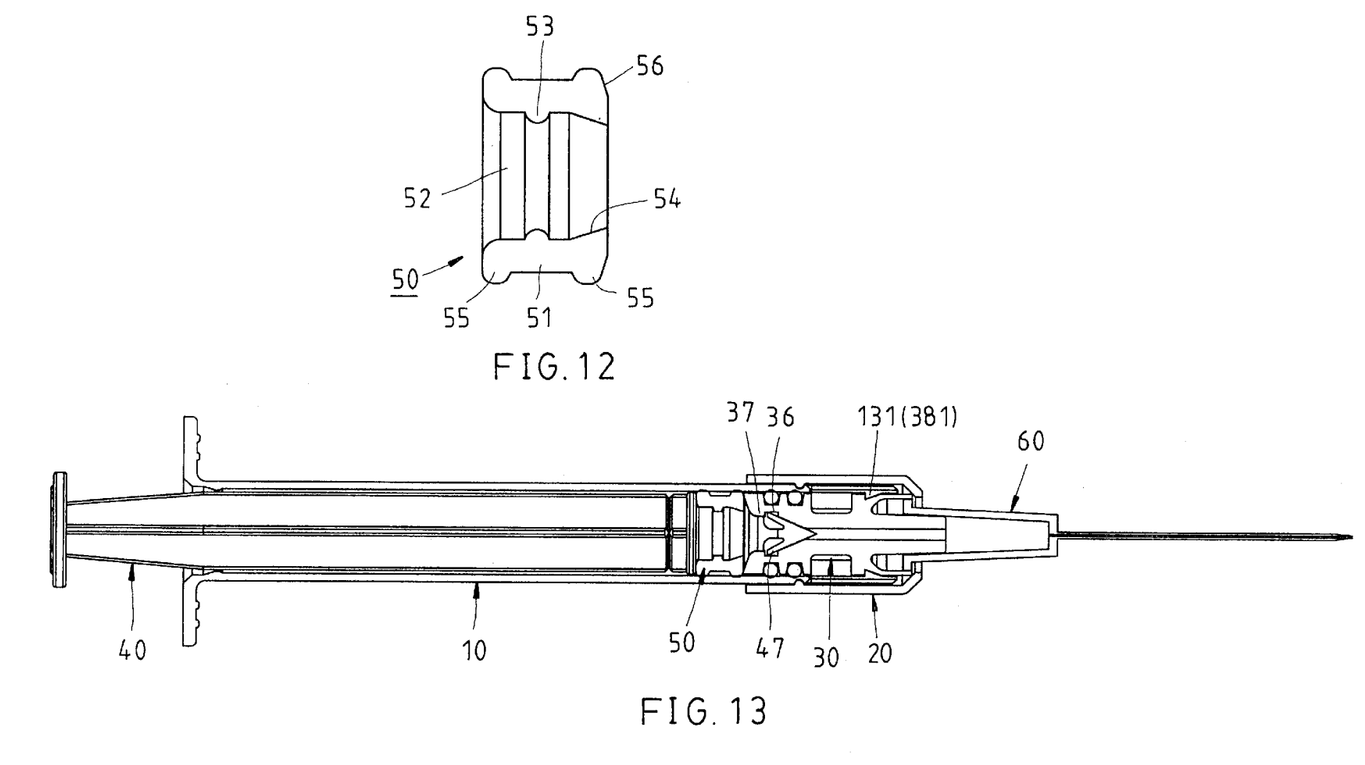
FIG. 12 shows a side sectional view of a stopper of the preferred embodiment of the present invention.
FIG. 13 shows a sectional schematic view of the plunger and the needle holder of the preferred embodiment of the present invention after injection.

As shown in FIG. 12, a stopper 50 has a circular body 51, which is provided in the center with a fitting hole 52 for fitting the neck 43 of the plunger 40, an inner protruded ring 53 formed in the inner edge of the fitting hole 52 and retained in the recessed slot 433 of the plunger 40, a tapered hole 54 disposed at the tapered rod 435 of the plunger 40, two protruded rings 55 formed respectively in the outer side of the circular body 51, an attachment face 56 formed at the end side edge thereof and capable of engaging the sunk hole 35 of the needle holder 30.

As shown in FIG. 3, the present invention is in the state of pre-injection. As the present invention is in use such that the injection is about to end, the two claws 47 of the plunger 40 are forced by the insertion hole 33 of the needle holder 30 to deform elastically to force the drug liquid to move forward.

As shown in FIG. 13, the safety hypodermic syringe of the present invention is in the state of post-injection such that the plunger 40 is located at the end of the range, and that each claw 47 has regained its original shape, and further that each claw 47 is now received in the open slot 36 of the needle holder 30, and further that each claw 47 engages the pull stop edge 37 of the needle holder 30.

Figure 14:
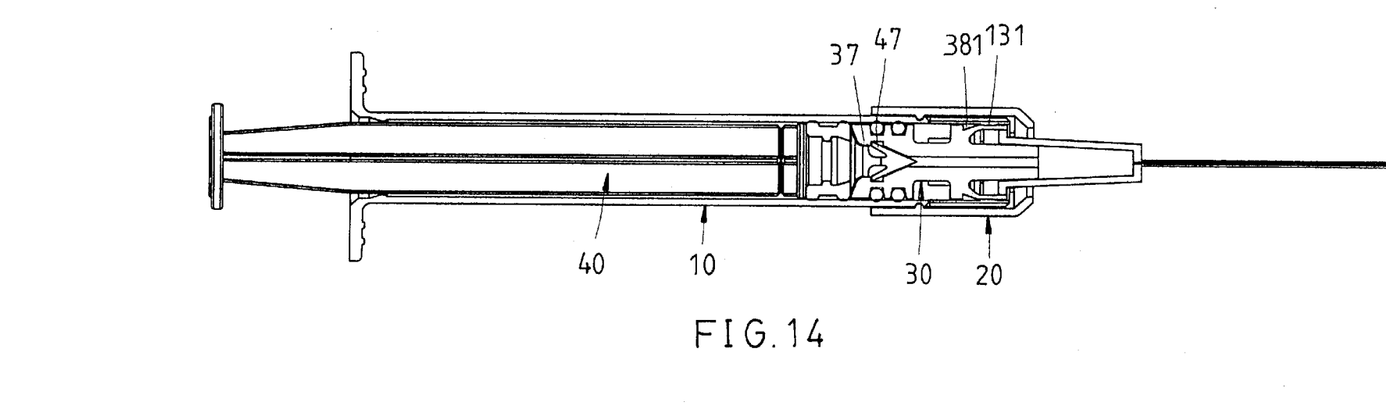
FIG. 14 is a sectional schematic view showing that the plunger of the preferred embodiment of the present invention is in an initial state of drawing the needle holder.

As shown in FIG. 14, the plunger of the present invention begins drawing the needle such that the plunger 40 is pulled to draw the needle holder 30 into the cylinder body 11.

In addition, the fitting head 61 of the needle 60 is enclosed in the protective sleeve 38 of the needle holder 30. As a result, the needle 60 is not detached at the time when it is collided with the barrel 10.

Figure 15:
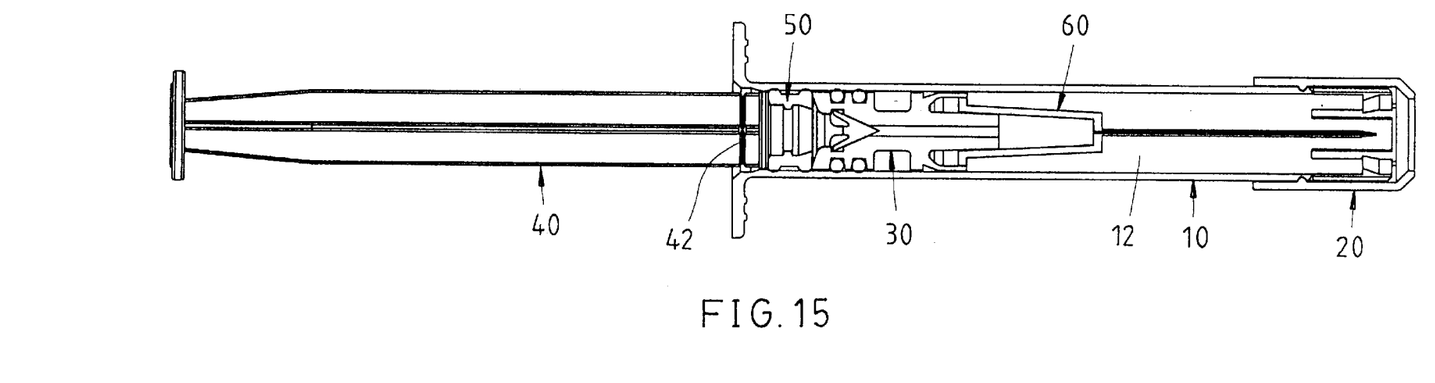
FIG. 15 is a sectional schematic view showing that the plunger of the preferred embodiment of the present invention is engaged with the needle holder so as to draw the needle holder.

As shown in FIG. 15, the hypodermic needle of the present invention is being drawn by the plunger such that the plunger 40 is stopped at the plunger stop edge 18 of the barrel 10, thereby enabling the plunger 40 to be bent to sever at the severing portion 42. As a result, the needle holder 30 and the hypodermic needle 60 remain in the receiving hole 12 of the barrel 10.

In light of intimate cooperation of the plunger 40 and the needle holder 30 of the present invention, the liquid drug residue is kept to a minimum. The plunger 40 is capable of effective retraction of the needle holder 30 along with the hypodermic needle 60 fastened to the needle holder 30.

The connection head of the plunger of the safety hypodermic syringe of the present invention may be either tapered or arcuate in shape. The outer side of the conical shape may be linear, concave, or convex.

The pull stop edge of the needle holder of the present invention is not necessarily formed by the open slot in communication with the external portion. The present invention may be devoid of the open slot. The pull stop edge may be formed by a greater receiving cell which is formed between the insertion hole and the inner tapered hole.

The present invention has several advantages over the prior art devices. In the first place, the plunger of the present invention is provided with the connection head capable of retaining the pull stop edge of the needle holder effectively. In addition, the liquid drug residue is kept to a minimum by virtue of the intimate cooperation of the connection head of the plunger with the inner tapered hole of the needle holder. Moreover, the retaining structure of the plunger and the needle holder of the present invention is simplified to facilitate the use of the present invention.

What is claimed is:

1. A safety hypodermic syringe comprising:

a barrel having a receiving hole;

a needle holder slidably and controllably disposed in said receiving hole of said barrel, said needle holder having an insertion hole, an inner tapered hole with a conical surface, a pull stop edge fixed between said insertion hole and said inner tapered hole, and a liquid transporting hole in communication with a hypodermic needle exiting from the inner tapered hole;

a plunger slidably engaged in the receiving hole of the barrel behind the needle holder, the plunger having a rod body;

an end of the rod body having a connection head with a conical front portion corresponding in shape to that of the inner tampered hole of the needle holder and a rear portion having two elastically deformable claws;

wherein during injection the plunger slides in the barrel so that the connection head passes through the insertion hole of the needle holder compressing the two elastically deformable claws until the conical front portion of the connection head is fully engaged against the conical surface of the inner tapered hole of the needle holder, wherein the two elastically deformable claws then are released to engage the pull stop edge of the needle holder so as to permit withdrawal of the plunger from the barrel with the needle holder and movement of the hypodermic needle into the receiving hole of the barrel.

2. The safety hypodermic syringe as defined in claim 1 further comprising an outer sleeve which is fitted over said barrel around said needle holder.

3. The safety hypodermic syringe as defined in claim 1, wherein said pull stop edge of said needle holder is formed by an open slot extending to said insertion hole.

4. The safety hypodermic syringe as defined in claim 1, wherein each claw of said plunger is of a sectoral shape.

5. The safety hypodermic syringe as defined in claim 1, wherein said plunger further has a stop plug disk which is formed between said rod body and said connection head; wherein said needle holder has a sunk hole cooperative with said stop plug disk.

6. The safety hypodermic syringe as defined in claim 1, wherein said plunger further has a neck, said syringe further comprising a stopper engaged to said neck.

7. The safety hypodermic syringe as defined in claim 6, wherein said neck of said plunger is provided with a recessed slot; wherein said stopper is provided with a protruded ring retainable in said recessed slot.

8. The safety hypodermic syringe as defined in claim 6, wherein said neck of said plunger is provided with a tapered rod; wherein said stopper is provided with a tapered hole to accommodate said tapered rod.

9. The safety hypodermic syringe as defined in claim 1, wherein said needle holder further has a protective sleeve which is fitted over a fitting head of said hypodermic needle to prevent detachment of said hypodermic needle at the time when said needle holder is pulled by said plunger.

10. The safety hypodermic syringe as defined in claim 1, wherein said needle holder is further provided with at least one outer circular groove to accommodate an O ring, which is engaged in said receiving hole of said barrel.

* * * * *